US012753422B2

(12) United States Patent
Han et al.

(10) Patent No.: US 12,753,422 B2
(45) Date of Patent: Oct. 6, 2026

(54) METHOD FOR PREPARING NATURAL NITRITE

(71) Applicant: CJ CHEILJEDANG CORPORATION, Seoul (KR)

(72) Inventors: Jin Hee Han, Seoul (KR); Sung Hoon Jo, Seoul (KR); Hyo Jung Yoon, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 465 days.

(21) Appl. No.: 18/265,060

(22) PCT Filed: Dec. 3, 2021

(86) PCT No.: PCT/KR2021/018242

§ 371 (c)(1),
(2) Date: Jun. 2, 2023

(87) PCT Pub. No.: WO2022/119386

PCT Pub. Date: Jun. 9, 2022

(65) Prior Publication Data

US 2024/0002887 A1 Jan. 4, 2024

(30) Foreign Application Priority Data

Dec. 4, 2020 (KR) ........................ 10-2020-0168855

(51) Int. Cl.
*C12P 3/00* (2006.01)
*A23B 2/788* (2025.01)

(52) U.S. Cl.
CPC ................ *C12P 3/00* (2013.01); *A23B 2/788* (2025.01); *C12Y 107/01002* (2013.01)

(58) Field of Classification Search
CPC . C12P 3/00; A23B 2/788; A23B 2/733; A23B 4/00; A23B 4/18; A23B 2/92; A23B 2/93; C12Y 107/01002; A23L 19/01; A23L 5/41; A23L 5/21; A23L 13/428; C09B 61/00; A23V 2002/00; A23V 2200/046; A23V 2250/21; A23V 2300/08; A23V 2300/10; A23V 2300/14
See application file for complete search history.

(56) References Cited

U.S. PATENT DOCUMENTS

| | | | |
|---|---|---|---|
| 9,062,293 | B2 | 6/2015 | Gilet et al. |
| 11,071,304 | B2 | 7/2021 | Husgen et al. |
| 2008/0305213 | A1 | 12/2008 | Husgen et al. |
| 2011/0300591 | A1 | 12/2011 | Gilet et al. |
| 2014/0242217 | A1 | 8/2014 | Husgen et al. |
| 2019/0297906 | A1 | 10/2019 | Hilhorst et al. |
| 2022/0022474 | A1 | 1/2022 | Husgen et al. |

FOREIGN PATENT DOCUMENTS

| | | | |
|---|---|---|---|
| EP | 2373175 | B1 | 9/2015 |
| JP | 2020-120670 | A | 8/2020 |
| KR | 10-2008-0104767 | A | 12/2008 |
| KR | 10-2013-0077632 | A | 7/2013 |
| KR | 10-2015-0043585 | A | 4/2015 |
| KR | 10-2017-0097891 | A | 8/2017 |
| KR | 10-2018-0031438 | A | 3/2018 |
| KR | 10-2019-0086383 | A | 7/2019 |
| KR | 10-2020-0075232 | A | 6/2020 |
| KR | 10-2197598 | B1 | 1/2021 |

OTHER PUBLICATIONS

Pandey K. N., "Y-irradiation activates biochemical systems: Induction of nitrate reductase activity in plant callus", Proc. Nati Acad. Sci. USA, 1982, vol. 79, pp. 5460-5464. (Year: 1982).*
Griffiths D. J., "Factors Affecting Nitrate Reductase Activity in Synchronous Cultures of Chlorella", The New Phytologist, 1979, vol. 82, pp. 427-437. (Year: 1979).*
Kaiser W.M. et al., "Acid-base-modulation of nitrate reductase in leaf tissues", Planta, 1995, vol. 196, pp. 1-6. (Year: 1995).*
Huber S.C. et al., "Post-translational regulation of nitrate reductase activity: a role for Ca 2+ and 14-3-3 proteins", Trends in Plant Science—Reviews, 1996, vol. 1, No. 12, pp. 432-438. (Year: 1996).*
Ferysiuk K. et al., "Reduction of Nitrite in Meat Products Through the Application of Various Plant-Based Ingredients"—Review, Antioxidants, 2020, 9, 711 (doi: 10.3390/antiox9080711), pp. 1-28. (Year: 2020).*
Kharytonov M. et al., "The Nitrates Nutrition Status Assessment and Management of the Horticultural Crops in the Steppe Zone of Ukraine", Annals of Faculty Engineering Hunedoara—International Journal of Engineering, Tome XVII, 2019, Fascicule 3 August, pp. 127-130. (Year: 2019).*
Park B.S. et al., "Arabidopsis nitrate reductase activity is stimulated by the E3 SUMO ligase AtSIZ1", Nature Communications, 2: 400 (DOI: 10.1038/ncomms1408 ), 2011, pp. 1-10. (Year: 2011).*
Ramarao C.S. et al., "Inactivation of Nitrate Reductase From Wheat and Rice Leaves", Phytochemistry, vol. 20, No. 7, pp. 1487-1491, 1981. (Year: 1981).*
Office Action issued Jul. 17, 2023 for counterpart Korean Patent Application No. 10-2020-0168855 (See English translation).
Krywult et al., "Method of Measurement of Nitrate Reductase Activity in Field Conditions", Journal of Ecological Engineering, vol. 14, No. 1, Jan. 2013, pp. 7-11.

(Continued)

*Primary Examiner* — Satyendra K Singh
(74) *Attorney, Agent, or Firm* — Morgan, Lewis & Bockius LLP

(57) ABSTRACT

The present application relates to a method of producing natural nitrite, the method including preparing an extract from a plant containing nitrate, activating nitrate reductase within the plant extract, and inactivating the nitrate reductase. According to the method of producing the natural nitrite, nitrite may be produced in a high concentration from natural raw materials without inoculation of reducing bacteria.

7 Claims, 1 Drawing Sheet

(56) References Cited

OTHER PUBLICATIONS

Meyer et al., "Is nitrate reductase a major player in the plant NO (nitric oxide) game?", Photosynthesis Research, vol. 83, 2005, pp. 181-189.
Partial Supplementary European Search Report issued in corresponding European Patent Application No. 21901074.1, dated Jun. 12, 2025.
Notice of Allowance issued in corresponding Korean Patent Application No. 10-2020-0168855, dated Jul. 4, 2024.
Barber et al., "Spinach Nitrate Reductase," Plant Physiology, 93: 537-540 (1990).
Kim et al., "Study of optimization of natural nitrite source production from spinach," Korean Journal of Food Science and Technology, 49 (4): 459-461 (2017) (see English abstract).
International Search Report issued in corresponding International Patent Application No. PCT/KR2021/018242 dated Mar. 18, 2022.
Rodriguez-Daza et al., "Obtaining nitrite from vegetables sources by fermentative process using nitrate-reducing bacteria *Sthaphylococcus carnosus* and *S. xylosus*," DYNA, 86 (210): 254-261 (2019).
Extended European Search Report issued in corresponding European Patent Application No. 21901074.1, dated 1 Dec. 5, 2025.

* cited by examiner

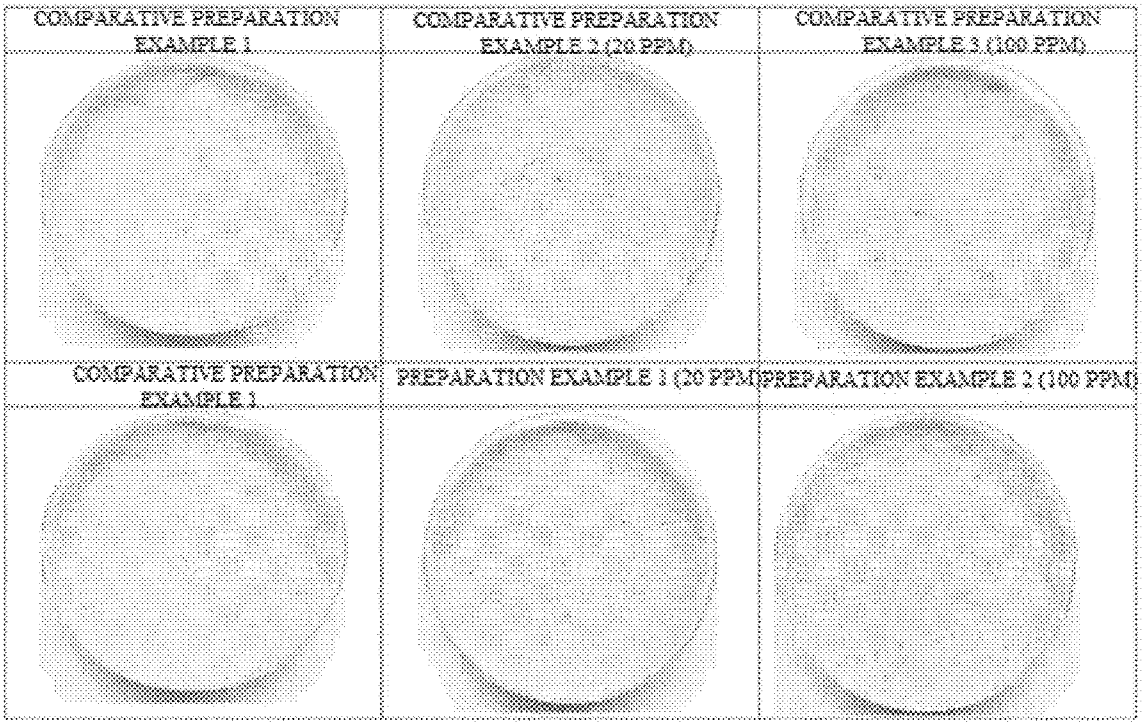
COMPARATIVE PREPARATION EXAMPLE 1
COMPARATIVE PREPARATION EXAMPLE 2 (20 PPM)
COMPARATIVE PREPARATION EXAMPLE 3 (100 PPM)
COMPARATIVE PREPARATION EXAMPLE 1
PREPARATION EXAMPLE 1 (20 PPM
PREPARATION EXAMPLE 2 (100 PPM)

METHOD FOR PREPARING NATURAL NITRITE

TECHNICAL FIELD

The present application relates to a method of producing natural nitrite.

BACKGROUND ART

Meat products such as ham and sausage processed using meat as a raw material are manufactured to have an inherent bright pinkish red or reddish color, and nitrite is added as a coloring agent to achieve color development of meat products. Nitrites allow meat products to exhibit a bright pinkish red color by reacting with myoglobin included in meat, and increase the shelf life of food products by inhibiting *C. botulinum* which produces toxin and preventing the growth of microorganisms.

However, in the case of synthetic nitrites commonly added as coloring agents, consumers are increasingly avoiding cured-meat products to which synthetic nitrites are added because synthetic nitrites are chemical synthetic additives, and accordingly, attempts have been made to produce and utilize nitrites from natural raw materials. As a method of producing natural nitrites, a method of obtaining nitrites by inoculating nitrate-rich plants or extracts thereof with reducing bacteria that have the ability to reduce nitrates to nitrites has been proposed.

KR 2018-0031438 discloses a method of producing natural nitrites by inoculating spinach extracts with *Lactobacillus farciminis* and performing fermentation, and "Study of optimization of natural nitrite source production from spinach" (KIM, Tae-Kyung et al. Korean J. Food Sci. Technol. vol. 49, no. 4, pp. 459-461(2017)) also discloses a method of inoculating *Staphylococcus carnosus* or various strains of *Lactobacillus* to produce natural nitrites by using spinach extracts. Inoculation of reducing bacteria is essentially used to produce natural nitrites. However, currently, there is a problem in that a process for producing natural plant extracts that satisfy a sufficient amount of nitrites, or a reduction technology is not secured in South Korea, and thus, plant extracts or reducing bacteria are mostly dependent on imports, and reducing bacteria must be cultured or purchased separately.

Accordingly, in the present application, a novel method of producing natural nitrite from plants without inoculating separate reducing bacteria is devised to complete the present invention.

DISCLOSURE

Technical Problem

An object of the present application is to provide a method of producing natural nitrite without inoculating reducing bacteria that have been used to produce conventional natural nitrite.

In addition, an object of the present application is to provide a natural nitrite-containing composition prepared through the above method.

In addition, an object of the present application is to provide a composition for producing natural nitrite.

Technical Solution

According to an aspect of the present application, there is provided a method of producing natural nitrite, the method including preparing an extract from a plant containing nitrate, activating nitrate reductase within the plant extract, and inactivating the nitrate reductase.

According to another aspect of the present application, there is provided a natural nitrite-containing composition prepared by the method of producing the natural nitrite.

According to another aspect of the present application, there is provided a composition for producing natural nitrite, the composition including a buffer solution containing a plant extract, wherein the plant extract contains nitrate.

According to another aspect of the present application, there is provided a meat product including the natural nitrite-containing composition and meat, wherein the meat product includes residual nitrite ion ($NO_2^-$) of 70 ppm or less.

A method of producing natural nitrite of the present application includes: preparing an extract from a plant containing nitrate, activating nitrate reductase within the plant extract, and inactivating the nitrate reductase.

The nitrite is a combination of a nitrite ion ($NO_2^-$) and a salt, and may be specifically sodium nitrite ($NaNO_2$), and the nitrate is a combination of a nitrate ion ($NO_3^-$) and a salt, and may be specifically sodium nitrate ($NaNO_3$).

The nitrite may be produced by nitrate reductase within the plant. Unlike the related art in which nitrite is produced by reducing bacteria by inoculating a nitrate-containing plant with external reducing bacteria, in a method of producing nitrite of the present application, the nitrite may be produced without inoculation of reducing bacteria by activating nitrate reductase present in a nitrate-containing plant or an extract of the plant. Therefore, there is an advantage in that a process for separately culturing reducing bacteria or a process for purchasing them may be omitted, such that nitrite may be produced in a more economical and easy way. The natural nitrite produced by the method of the present application has an excellent color development effect when applied to meat products, and costs, facilities, labor, and the like required to produce the natural nitrite may be reduced. In addition, since there is no need to go through a process for inoculating reducing bacteria, there are advantages in that there is no concern about problems such as generation of unintended substances that may be caused by reducing bacteria, and there is no need for a process to remove reducing bacteria or by-products produced therefrom.

The plant may be at least one selected from the group consisting of spinach, lettuce, Chinese cabbage, head lettuce, cabbage, young radish, sesame leaf, chicory, radish leaf, radish, crown daisy, kale, leaf mustard, leek, water parsley, and red beet, but is not limited thereto, and any plant that contains nitrate may be utilized. The plant may include nitrate in a concentration of 3,000 ppm or more, for example, 3,100 ppm or more, 3,200 ppm or more, 3,300 ppm or more, 3,500 ppm or more, 4,000 ppm or more, 4,500 ppm or more, 5,000 ppm or more, 3,000 ppm to 10,000 ppm, 3,200 ppm to 8000 ppm, 3,500 ppm to 7,000 ppm, or 4,000 ppm to 6,000 ppm, but is not limited thereto, and the plant may be utilized as long as the plant includes nitrate in a concentration sufficient to allow a nitrite conversion reaction to occur.

The extraction is a process for releasing a component included in the plant to the outside, wherein the plant may be squeezed or crushed. The squeezing may include using conventional juicers, juicers for greens, or the like to obtain juice from plants. The crushing may include crushing or milling plants to obtain liquid within the plants and a plant body.

The plant extract may include nitrate and nitrate reductase within the plant. When an extract is prepared through the extraction method as described above, there is an advantage in that the activity of nitrate reductase included in the extract may be maintained without loss or inhibition. For example, there is an effect of preventing inhibition of the activity of nitrate reductase, which may be caused by heat, a solvent, or an enzyme introduced from the outside.

The nitrate reductase is an enzyme that have the ability to reduce nitrate to nitrite, and the activating of the nitrate reductase may include inducing the activity of converting nitrate to nitrite or increasing a conversion rate. As the nitrate reductase is activated, a process for fermenting the plant extract is performed, and thus, nitrite may be produced.

In the present application, the term "fermentation" refers to a series of metabolic processes in which organic compounds are changed by enzyme action.

The activating of the nitrate reductase may include maintaining a pH range through a buffer system. Specifically, the maintaining of the pH range may include maintaining a pH within a range of pH 6 to pH 9, and specifically, within a range of pH 6.5 to pH 9, pH 6.5 to pH 8.5, pH 6.5 to pH 8, pH 6.5 to pH 7.5, or pH 6.5 to pH 7. In the case of going through a metabolic process, by-products thus produced may reduce the pH, thereby reducing the activity of the nitrate reductase. Therefore, in the case of maintaining the pH within the above range, the activity of the nitrate reductase may not be reduced, and a nitrite conversion rate may be maintained high.

The nitrite conversion rate, when the plant extract is fermented for 10 hours, may be up to 95%, and specifically, the nitrite conversion rate may be 95% or less, 94% or less, 93% or less, 92% or less, 91% or less, 90% or less, 89% or less, 88% or less, 85% or less, 80% or less, 75% or less, 72% or less, 70% or less, 65% or less, 60% or less, 40% to 95%, 45% to 95%, 50% to 95%, 55% to 94%, 60% to 93%, 65% to 92%, or 70% to 90%.

The activating of the nitrate reductase may include fermenting the plant extract in a phosphate buffer solution or a carbonate buffer solution. The buffer solution may maintain the pH within a range of pH 7 to pH 9, and specifically, within a range of pH 7.5 to pH 9, pH 7.5 to pH 8.5, pH 8 to pH 9, or pH 8 to pH 8.5.

The phosphate buffer solution may be a buffer solution including $NaH_2PO_4$ and $Na_2HPO_4$, and the carbonate buffer solution may be a buffer solution including $Na_2CO_3$ and $NaHCO_3$. The phosphate buffer solution may be in a concentration of 0.05 M to 0.5 M, and specifically, 0.08 M to 0.4 M, 0.1 M to 0.3 M, 0.1 M to 0.25 M, 0.1 M to 0.2 M, or 0.08 M to 0.15 M. The carbonate buffer solution may be in a concentration of 0.005 M to 0.1 M, and specifically, 0.005 M to 0.1 M, M to 0.07 M, 0.01 M to 0.05 M, 0.008 M to 0.04 M, 0.01 M to 0.04 M, or 0.025 M to 0.035 M. When the plant extract is fermented in the phosphate buffer solution and/or the carbonate buffer solution, a sufficient buffering effect on a change in pH may be exhibited, and at the same time, the efficiency of the fermentation may increase, thereby increasing a nitrite conversion rate attributed to the nitrate reductase.

The activating of the nitrate reductase may include maintaining a temperature of 20° C. to and specifically, 25° C. to 40° C., 30° C. to 40° C., or 30° C. to 35° C., and may include stirring at a stirring speed of 150 rpm to 250 rpm.

The method of producing the natural nitrite of the present application is to produce the natural nitrite by activating nitrate reductase present in a plant, and in particular, a method of increasing the activity of a fermentation process for converting nitrate to nitrite has been newly identified. The method of producing the natural nitrite of the present application has an effect of obtaining a large amount of nitrite simply by fermenting the plant without separately inoculating reducing bacteria from the outside.

The inactivating of the nitrate reductase may include heating the plant extract to a temperature of 55° C. to 95° C. Specifically, the inactivating of the nitrate reductase may include heating to a temperature of 55° C. to 90° C., 60° C. to 95° C., 60° C. to 90° C., 65° C. to 85° C., 55° C. to 85° C. to 95° C., or 59° C. to 61° C. When the heating is performed to a temperature within the range, there is an advantage in that the amount of loss of nitrite produced while the activity of the nitrate reductase sufficiently disappears may be minimized.

The method of producing the natural nitrite may further include filtering and/or sterilizing the plant extract after the inactivating of the nitrate reductase. The filtration is removal of suspended solid particles from the plant extract to obtain only a water-soluble supernatant, excluding sediment, and is a process for removing foreign substances or fine substances other than nitrite. The filtration may be performed by using a filter such as cotton or nylon, for example, a filter of 0.2 μm to 5 μm, to filter out particles, or by using cryofiltration or centrifugation, but is not limited thereto. The sterilization may be application of high-temperature heat, for example, heating to a temperature of 90° C. to 105° C. or 95° C. to 100° C.

The method of producing the natural nitrite may further include concentrating the plant extract after the inactivating of the nitrate reductase. The concentrating of the plant extract may include increasing a nitrite concentration of a nitrite-containing plant extract through the fermentation, and a concentrate thus obtained is more easily used by adding the concentrate to meat products. The concentration may include vacuum concentration, plate-type concentration, thin-film concentration, but is not limited thereto, and for example, may be performed by using a centrifugal thin-film concentrator.

The method of producing the natural nitrite of the present application may further include drying the plant extract after the inactivating of the nitrate reductase.

The drying of the plant extract may be a process in which a nitrite-containing plant extract is prepared in the form of powder through fermentation to increase a nitrite concentration. The drying of the plant extract may include lyophilization or spray drying. The lyophilization may include freezing at a low temperature without adding an excipient, for example, pre-freezing at a temperature of −75° C. to −65° C., and then raising a temperature from −40° C. to 30° C. The spray drying may include mixing a nitrite-containing plant extract with an excipient such as maltodextrin and then drying the mixture. In this case, the plant extract and the maltodextrin may be mixed in a ratio of 80:20 to 95:5, and specifically, in a ratio of 83:17 to 93:7, 85:15 to 92:8, 85:15 to 90:10, 88:12 to 92:8, or 89:11 to 91:9. In the case of performing spray drying by mixing with an excipient in the above ratio, or lyophilization, there is an advantage in that final powder includes a large amount of nitrite.

The method of producing the natural nitrite of the present application may not include inoculating reducing bacteria having nitrate-reducing activity.

A natural nitrite-containing composition of the present application may be prepared by the method of producing the natural nitrite.

The natural nitrite-containing composition of the present application may include nitrite in a concentration of 700 ppm or more. Specifically, the nitrite may be included in a concentration of 700 ppm or more, 750 ppm or more, 800 ppm or more, 1,000 ppm or more, 2,000 ppm or more, 2,500 ppm or more, 3,000 ppm or more, 5,000 ppm or more, 8,000 ppm or more, ppm or more, 20,000 ppm or more, 30,000 ppm or more, 40,000 ppm or more, 50,000 ppm or more, 60,000 ppm or more, 70,000 ppm or more, 80,000 ppm or more, 90,000 ppm or more, 100,000 ppm or more, 110,000 ppm or more, 120,000 ppm or more, 130,000 ppm or more, 150,000 ppm or more, 180,000 ppm or more, or 200,000 ppm or more. As the nitrite is included in the above concentration, the composition of the present application, when applied to meat products, may allow the meat products to exhibit an inherent reddish color, and may exhibit a color development effect at a level superior or similar to that exhibited when synthetic nitrite is used or when natural nitrite is produced by another method.

The natural nitrite-containing composition of the present application may include free sugar in a concentration of 1,000 ppm or less, and the free sugar may include lactose.

Specifically, the free sugar may be included in a concentration of 1,000 ppm or less, 900 ppm or less, 800 ppm or less, 700 ppm or less, 500 ppm or less, 300 ppm or less, 200 ppm or less, 100 ppm or less, or 50 ppm or less. Among free sugars, reducing sugars may cause browning, after being applied to products, in a process of sterilizing them at high temperatures, thereby negatively affecting the appearance of the products. As the natural nitrite-containing composition of the present application includes the free sugar in a concentration in the above range, when applied to meat products, the natural nitrite-containing composition may have an effect of reducing browning caused by the free sugar, which may result in a synergistic effect with respect to color and appearance improvement of products together with a color development effect attributed to nitrite.

The natural nitrite-containing composition of the present application may include fructose in a concentration of 1,000 ppm or less, or may not include glucose and sucrose.

The natural nitrite-containing composition of the present application may further include at least 8 amino acids selected from the group consisting of aspartic acid, glutamic acid, glycine, alanine, valine, methionine, isoleucine, leucine, tyrosine, phenylalanine, lysine, and arginine in a concentration of 500 ppm or more. Specifically, the amino acids may be included in a concentration of 500 ppm or more, 600 ppm or more, 800 ppm or more, 1,000 ppm or more, 1,500 ppm or more, 2,000 ppm or more, 2,500 ppm or more, 3,000 ppm or more, 5,000 ppm or more, 7,000 ppm or more, 10,000 ppm or more, 12,000 ppm or more, 15,000 ppm or more, 17,000 ppm or more, 20,000 ppm or more, or 25,000 ppm or more. A nitrite-containing composition prepared by inoculating reducing bacteria may include amino acids in an amount less than the above range, and more specifically, may not include amino acids such as glycine, methionine, isoleucine, leucine, tyrosine, lysine, histidine, and arginine, and thus, the amino acid concentration range and the amino acid type of the composition of the present application may be one of characteristics distinct from the nitrite-containing composition prepared by inoculating reducing bacteria. In addition, as the composition of the present application includes various types of amino acids such as those described above in relatively high concentrations, positive effects may be exhibited in terms of nutrition and taste. For example, amino acids such as aspartic acid, glutamic acid, and glycine are known to have umami taste, and thus, when the composition of the present application is applied to meat products, advantageous effects may be exhibited in terms of flavor. In particular, the natural nitrite-containing composition of the present application may be applied to meat products and utilized for the purpose of inducing color development of the meat products, and considering objects to be applied are food products, the effects produced by the inclusion of amino acids such as those described above may exhibit a desirable synergistic effect together with a color development effect of the present application.

The natural nitrite-containing composition of the present application may further include at least one nucleic acid-based compound selected from the group consisting of hypoxanthine, guanosine, xanthine, inosine, xanthosine, and IMP.2Na·7.5$H_2O$. The natural nitrite-containing composition may not include adenine and/or AMP.2Na. A nitrite-containing composition prepared by inoculating reducing bacteria may not include hypoxanthine, guanosine, xanthine, inosine, xanthosine, and IMP.2Na·7.5$H_2O$, but may include adenine and AMP.2Na.

The natural nitrite-containing composition may further include acetic acid in a concentration of 1,000 ppm or more. Specifically, the acetic acid may be included in a concentration of 1,000 ppm or more, 2,000 ppm or more, 3,000 ppm or more, 5,000 ppm or more, 7,000 ppm or more, 10,000 ppm or more, 12,000 ppm or more, 20,000 ppm or more, 30,000 ppm or more, 40,000 ppm or more, or 45,000 ppm or more. In addition, the composition may include succinic acid. However, a nitrite-containing composition prepared by inoculating reducing bacteria may include 300 ppm or less of acetic acid, or may include only a small amount of succinic acid.

The natural nitrite-containing composition may include γ-aminobutyric acid (GABA) in a concentration of 25 mg/L or more. Specifically, the GABA may be in a concentration of 25 mg/L or more, 50 mg/L or more, 100 mg/L or more, 200 mg/L or more, 500 mg/L or more, 900 mg/L or more, 1,000 mg/L or more, 1,500 mg/L or more, 1,700 mg/L or more, 2,000 mg/L or more, or 2,100 mg/L or more. A nitrite-containing composition prepared by inoculating reducing bacteria may include 100 ppm or less of GABA, or may include an extremely small amount of GABA.

The natural nitrite-containing composition of the present application may not include reducing bacteria having nitrate-reducing activity.

The natural nitrite-containing composition of the present application may be in the form of powder, and in this case, may include nitrite in a concentration of 100,000 ppm or more. The powder may be prepared by freeze-drying (lyophilization) or spray drying. When the composition of the present application is in the form of powder, the composition may include nitrite in a higher concentration and has an advantage of being easy to be applied to meat products. In addition, the composition in the form of powder has advantages in terms of storage and distribution processes.

A composition for producing natural nitrite of the present application may include a buffer solution containing a plant extract, and the plant extract contains nitrate.

The buffer solution maintains a pH of the composition within a range of pH 7 to pH 9.

The plant is the same as the plant described in connection with the method of producing the natural nitrite, may be at least one selected from the group consisting of spinach, lettuce, Chinese cabbage, head lettuce, cabbage, young radish, sesame leaf, chicory, radish leaf, radish, crown daisy, kale, leaf mustard, leek, water parsley, and red beet, and may include nitrate in a concentration of 3,000 ppm or more.

The buffer solution is the same as the buffer solution described in connection with the method of producing the natural nitrite, and the buffer solution may be a phosphate buffer solution including $NaH_2PO_4$ and $Na_2HPO_4$ or a carbonate buffer solution including $Na_2CO_3$ and $NaHCO_3$.

The natural nitrite-containing composition may be used to induce color development of meat products and manufacture meat products. A composition for manufacturing the meat products may include pork, pork fat, and purified water, and its components and amount may vary depending on meat products. The composition for manufacturing the meat products may include the natural nitrite-containing composition in an amount of 5 wt % or less. Specifically, the natural nitrite-containing composition may be included in an amount of 4 wt % or less, 3 wt % or less, 2 wt % or less, 1 wt % or less, 0.5 wt % or less, 0.3 wt % or less, 0.2 wt % or less, 0.1 wt % or less, 0.08 wt % or less, 0.05 wt % or less, 0.03 wt % or less, or 0.01 wt % or less. The amount may vary depending on the amount of nitrite within a natural coloring agent, but since a natural coloring agent composition according to the present invention includes a high concentration of sodium nitrite, the amount of the natural coloring agent composition may be reduced, and as described above for the natural nitrite-containing composition, the natural nitrite-containing composition has an excellent color development effect when applied to meat products, allowing the meat products to exhibit their inherent bright pinkish red or reddish color. Therefore, the natural nitrite-containing composition may be usefully utilized for developing a color of meat products.

A meat product of the present application includes the natural nitrite-containing composition and meat. The meat product may include residual nitrite ion ($NO_2$) of 70 ppm or less.

As described above for the natural nitrite-containing composition, the natural nitrite-containing composition has an excellent color development effect when applied to meat products, allowing the meat products to exhibit their inherent bright pinkish red or reddish color. In addition, the natural nitrite-containing composition is prepared by using natural raw materials such as plants, and may be used as a substitute for synthetic nitrite. Therefore, the inclusion of the natural nitrite-containing composition in the meat product of the present application has an excellent effect in that meat may be allowed to exhibit a desired bright pinkish red or reddish color to have an appearance that satisfies preferences of consumers and stimulates their appetites.

The residual nitrite ion may be specifically in a concentration of 70 ppm or less, 65 ppm or less, 60 ppm or less, 55 ppm or less, 50 ppm or less, 40 ppm or less, 30 ppm or less, 20 ppm or less, 15 ppm or less, 10 ppm or less, 5 ppm or less, 2 ppm or less, or 1 ppm or less. Since nitrite ions may have the potential to have negative effect on health, when the amount of the residual nitrite ion is within the above range, there is an advantage in that a sufficient color development effect may be exhibited in meat products, and at the same time, adverse effects on health may be minimized.

The present application provides a method of developing a color of meat. The method of developing the color of the meat of the present application includes mixing the natural nitrite-containing composition with a meat raw material. As described above for the natural coloring agent composition, the natural coloring agent composition has an excellent color development effect when applied to meat products, allowing the meat products to exhibit their inherent bright pinkish red or reddish color. Therefore, meat may be colored to have a desired level of meat color by mixing the natural coloring agent composition with the meat raw material.

Advantageous Effects

According to a method of producing natural nitrite of the present application, nitrite may be produced from natural plant raw materials to replace synthetic nitrite while being capable of developing a color of meat by being applied to meat products. According to a method of producing natural nitrite of the present application, nitrite is produced through fermentation without external reducing bacteria by activating enzymes within a nitrate-containing plant without inoculation of reducing bacteria. Therefore, a process for culturing or purchasing reducing bacteria may be omitted, and thus, there is an economically advantageous effect, and there is an advantage in that there is no concern about production of unintended by-products due to reducing bacteria.

The natural nitrite produced by the above method may induce color development of meat products to a level similar to that of meat products in which synthetic nitrite is used, and attributed to a small amount of free sugars, may prevent browning caused by reducing sugar, thereby significantly improving the appearance quality of meat products. In addition, a large amount of amino acids included in the natural nitrite-containing composition prepared by the method of the present application may improve the taste quality of meat products, and considering that the composition is applied to food products, an excellent synergistic effect may be expected.

However, the effects of the present application are not limited to the effects mentioned above, and other effects not mentioned will be clearly understood by those skilled in the art from the following description.

DESCRIPTION OF DRAWING

FIG. 1 shows images captured by observing appearances of model meat products (Preparation Example 1 and Preparation Example 2) made by mixing meat with a nitrite-containing composition prepared by fermenting spinach without inoculation of reducing bacteria, model meat products (Comparative Preparation Examples 2 and 3) to which synthetic nitrite was added, and a model meat product (Comparative Preparation Example 1) to which nitrite was not added.

MODE FOR INVENTION

Hereinafter, the present application will be described in detail by Examples.

However, the following Examples specifically illustrate the present application, and the description of the present application is not limited by the following Examples.

Example 1

Production of Large Amount of Natural Nitrite without Using Reducing Bacteria

Unlike conventional methods of producing nitrite by using reducing bacteria that have the ability to reduce nitrate to nitrite, in the present application, a method of producing a large amount of natural nitrite by activating nitrate reductase contained in plants without using the reducing bacteria is newly invented.

[1-1] Confirmation of Effect of Nitrate Reductase in Increasing Nitrite Conversion Rate According to pH Control Among plants containing a large amount of nitrate and having nitrate reductase, spinach was selected, and activation of its nitrate reductase was induced to produce nitrite. products were manufactured with nitrate of 100 ppm or less and nitrite of 100 ppm or less, respectively.

pH Control Using Phosphate Buffer Solution System ($NaH_2PO_4$, $Na_2HPO_4$)

First, a phosphate buffer solution system including $NaH_2PO_4$ and $Na_2HPO_4$ was formed, the final pH of a buffer solution was adjusted to be 8.3, and buffer solutions with concentrations of 0.1 M and 0.2 M were each reacted with the fermented spinach prepared as described above. The initial pH of the squeezed spinach extract was 6.58, and the pH and nitrite conversion rate that were changed as a nitrate-to-nitrite conversion reaction progressed under the buffer solution system are shown in Table 1.

TABLE 1

| Concentration | Item | Extract | 1 hour | 2 hours | 3 hours | 4 hours | 5 hours | 6 hours | 7 hours | 8 hours | 9 hours | 10 hours |
|---|---|---|---|---|---|---|---|---|---|---|---|---|
| 0.1M | pH | 6.58 | 7.42 | 7.42 | 7.33 | 7.26 | 7.10 | 6.90 | 6.65 | 6.48 | 6.35 | 6.13 |
| | Conversion rate (%) | 0% | 1% | 1% | 2% | 7% | 17% | 23% | 41% | 57% | 57% | 56% |
| 0.2M | pH | 6.58 | 7.55 | 7.47 | 7.47 | 7.35 | 7.23 | 7.05 | 6.82 | 6.61 | 6.50 | 6.41 |
| | Conversion rate (%) | 0% | 1% | 1% | 1% | 2% | 6% | 15% | 23% | 35% | 42% | 38% |

In addition to spinach, lettuce, Chinese cabbage, head lettuce, cabbage, young radish, sesame leaf, chicory, radish leaf, radish, crown daisy, kale, leaf mustard, leek, water parsley, and red beet may be used, and plants in which a concentration of nitrate is 3,000 ppm or more may be used.

With respect to the spinach, while pH conditions were changed, the activation of the nitrate reductase and fermentation was induced without inoculation of reducing bacteria from outside, and then the amount of nitrite was measured to identify whether the nitrate was converted to nitrite by the nitrate reductase within the spinach.

Specifically, Korean spinach (3,000 ppm or more of nitrate) was washed in running water to remove soil and foreign substances and then squeezed by using a conventional juicer for greens to thereby obtain a spinach extract. The spinach extract was fermented under a condition of impeller 200 rpm while pH conditions were changed, at a temperature of 20° C. to 40° C. in a 2 L fermenter (Marado-PDA, BIOCNS Co., South Korea), and a change in pH and changes in concentrations of nitrate and nitrite over time were measured. The amounts of nitrate and nitrite were analyzed by HPLC. A sample was diluted according to a detection concentration, and a supernatant thereof was filtered using a 0.25 μm syringe filter so as to be used as an analysis sample, and Eclipse XDB-C18 (4.6×250 mm, 5 μm) was maintained at 40° C. and used as a column. A detector was a DAD detector and a 210 nm wavelength was used, a mobile phase A solution used was methanol, a mobile phase B solution used was 10 mM octylamine, and in a gradient mode, 0 min, 80% B, 15 min, 50% B, 20 min, 50% B, and 25 min, 80% B were flowed at a flow rate of 1.0 mL/min and injected in an amount of 20 μL, for analysis. Standard As a result, at the beginning of the reaction, the pH was measured to be about 7.5, but as the fermentation progressed, the pH gradually decreased, and a buffering effect of pH was shown in both 0.1 M and 0.2 M buffer solutions. In addition, in the case of the 0.1 M buffer solution, the nitrite conversion rate was measured to be 56% at 10 hours into the reaction. The 0.2 M buffer solution had a smaller change in pH and thus a better buffering effect than the 0.1 M buffer solution, but the nitrite conversion rate was measured to be 38% at 10 hours into the reaction, and thus, the reaction was delayed compared to the case where the 0.1 M buffer solution was used.

Given the above result, it was confirmed that the pH had a major effect on the activity of the nitrate reductase and the nitrite conversion rate, and accordingly, a buffer system capable of adjusting the appropriate pH should be applied in order to produce and obtain a larger amount of nitrite. In addition, it was confirmed that a large amount of nitrite could be effectively produced when the concentration of the phosphate buffer solution including $NaH_2PO_4$ and $Na_2HPO_4$ was adjusted and applied.

pH Control Using Carbonate Buffer Solution System ($Na_2CO_3$, $NaHCO_3$)

Next, a carbonate buffer solution system ($Na_2CO_3$—$NaHCO_3$) was formed, the final pH was adjusted to be 9.5, and the spinach extract prepared as described above was fermented by using each of buffer solutions with concentrations of 0.01 M, 0.03 M, and 0.05 M. The initial pHs of the squeezed spinach extract were 6.21, 6.43, and 6.27, respectively, and the pHs and nitrite conversion rates that were changed as a nitrate-to-nitrite conversion reaction progressed under the buffer solution system are shown in Table 2.

TABLE 2

| Concentration | Item | Extract | 1 hour | 2 hours | 3 hours | 4 hours | 5 hours | 6 hours | 7 hours | 8 hours | 9 hours | 10 hours |
|---|---|---|---|---|---|---|---|---|---|---|---|---|
| 0.01M | pH | 6.21 | 7.86 | 7.86 | 7.83 | 7.80 | 7.54 | 7.04 | 6.75 | 6.50 | 6.32 | 6.25 |
| | Conversion rate (%) | 0% | 1% | 1% | 2% | 2% | 15% | 26% | 35% | 43% | 48% | 52% |
| 0.03M | pH | 6.43 | 8.12 | 8.09 | 8.09 | 8.06 | 7.97 | 7.73 | 7.17 | 6.71 | 6.57 | 6.51 |
| | Conversion rate (%) | 0% | 1% | 1% | 2% | 2% | 7% | 36% | 42% | 75% | 72% | 72% |
| 0.05M | pH | 6.27 | 9.08 | 9.06 | 9.05 | 9.02 | 8.97 | 8.68 | 8.19 | 7.88 | 7.72 | 7.63 |
| | Conversion rate (%) | 0% | 1% | 1% | 2% | 2% | 2% | 2% | 3% | 6% | 9% | 13% |

As a result, in the case of the 0.01 M buffer solution, the pH decreased gently, and the nitrite conversion rate was measured to be 52% at 10 hours into the reaction. In the case of the M buffer solution, the pH was 6.51 and the conversion rate was measured to be 72% at 10 hours into the reaction, indicating the best nitrite conversion effect. In the case of the 0.05 M buffer solution, the pH was changed to strong alkalinity, deviating from the range in which the nitrate reductase is active and thus resulting in a significant decrease in the nitrite conversion rate.

Given the above result, it was confirmed that when the 0.03 M carbonate buffer solution was used, the nitrate-to-nitrite conversion efficiency was the best, and in spite of not inoculating reducing bacteria, a large amount of nitrite could be successfully produced. When a pH decreases due to metabolites that generate as a conversion reaction attributed to nitrate reductase progresses, the activity of the nitrate reductase may be inhibited, and the nitrite production efficiency may decrease. In the present application, a composition including a large amount of nitrite could be prepared by constructing a buffer solution system by which conversion to nitrite could be most efficiently achieved by solving these problems.

Optimization of Nitrite Conversion Reaction Conditions

Through the above experiments, it was confirmed that when the 0.03 M carbonate buffer solution system was used, the nitrite conversion rate was relatively higher, and thus, based on this, nitrite conversion reaction conditions were optimized, and a conversion rate according to a reaction time was measured and is shown in Table 3. The initial pH was within a range of 8.5 to 9.0, the M $Na_2CO_3$—$NaHCO_3$ buffer solution was used, and the reaction was performed at a stirring speed of 200 rpm.

As a result, it was confirmed that the pH gradually decreased as the reaction progressed, but a buffering effect attributed to the buffer solution was sufficiently shown, and the conversion rate increased to about 90% at about 7 hours into the reaction, indicating a significantly excellent conversion effect.

[1-2] Confirmation of Nitrite Amount Increase Effect

In Example 1-1, the fermented spinach including a large amount of nitrite could be obtained by increasing the activity of the nitrate reductase within the spinach extract and the conversion rate by adjusting the pH conditions. The concentration of nitrite contained in the fermented spinach may be further increased through concentration and drying processes. In these processes, some nitrite may be lost, but it was confirmed which type of drying could obtain a high concentration of nitrite attributed to the least loss of nitrite by controlling drying methods and conditions.

First, an inactivation process was performed to remove the activity of the nitrate reductase in the fermented spinach prepared through the process of Example 1-1. After the fermented spinach was heated to a high temperature of 60° C. or more to inactivate the enzyme, 5% diatomaceous earth was added by using a filter press (JUNGDO 1000, JUNGDO Co., South Korea) and subjected to filtration using a 15 cc filter cloth for a first filtration, followed by a second filtration using a 5 μm MF filter to additionally remove residual diatomaceous earth and fine substances. Next, sterilization was performed at a temperature of 95-100° C. for 1 minute and 30 seconds by using a UHT sterilizer. In addition, as concentration using a centrifugal thin-film concentrator was

TABLE 3

| | Extract | 0 hour | 1 hours | 2 hours | 3 hours | 4 hours | 5 hours | 6 hours |
|---|---|---|---|---|---|---|---|---|
| pH | 6.09 | 8.99 | 8.77 | 8.65 | 8.04 | 7.34 | 7.19 | 7.02 |
| Nitrate (ppm) | 3,273 | 3,259 | 3,012 | 3,454 | 3,346 | 2,545 | 1,761 | 1,014 |
| Nitrite (ppm) | 0 | 0 | 0 | 0 | 297 | 933 | 1,556 | 2,082 |
| Conversion rate (%) | 0% | 0% | 0% | 0% | 9% | 29% | 48% | 64% |

| | 6.5 hours | 7 hours | 7.5 hours | 8 hours | 8.5 hours |
|---|---|---|---|---|---|
| pH | 6.83 | 6.74 | 6.70 | 6.60 | 6.54 |
| Nitrate (ppm) | 438 | 51 | 0 | 0 | 0 |
| Nitrite (ppm) | 2,602 | 2,874 | 2,948 | 2,897 | 2,899 |
| Conversion rate (%) | 79% | 88% | 90% | 89% | 89% |

performed, a concentrate of a nitrite-containing composition of the present application was prepared (Table 4).

TABLE 4

| | Nitrite (ppm) |
|---|---|
| Concentration concentration (27.5 Brix) | 34,728 |

Next, powders of spinach extract were prepared through spray-drying and lyophilization methods by different spraying methods for the concentrate, and the concentrations of nitrite contained therein were measured and compared. In the case of spray drying, the solid content was adjusted to a level of 35-38 Brix by mixing maltodextrin with the concentrate. Ratios of the spinach concentrate to the maltodextrin were respectively set to 85:15, 88:12, and 90:10, followed by spray drying (in let temperature: 180° C., out let temperature: 90° C., sample injection speed: 10 mL/min). In the case of lyophilization, the concentrate was pre-frozen in a deep freezer at −70° C. without adding an excipient thereto and then subjected to using a lyophilizer. As conditions for the lyophilization, drying was performed for 72 hours with a vacuum degree of 20 kPa and with the temperature inside the chamber slowly raised from −40° C. to 30° C. The concentrations of nitrite included in the spray-dried powders (SD powders) in the above three ratios and the lyophilized powder (FD powder) were measured and are shown in Table 5.

TABLE 5

| Composition | Nitrite (ppm) |
|---|---|
| SD powder (85:15) | 67,806 |
| SD powder (88:12) | 72,659 |
| SD powder (90:10) | 80,780 |
| FD powder (100) | 104,917 |

prepared through the spray drying, but since the lyophilization is a method of purely evaporating water without adding an excipient, a high amount of nitrite may be maintained, and as in the experimental result, it was confirmed that the powder prepared through the lyophilization had higher concentration of nitrite than other spray-dried powders.

Given the above result, it was confirmed that the lyophilization method could yield a large amount of powder having a higher concentration of nitrite than the spray-drying method, and it was confirmed that it was possible to prepare and use the powder in a form that could be used in a small amount such that other effects other than the function as a coloring agent could be minimized by using the high-concentration powder when the powder of the fermented spinach was to be applied to a product.

Example 2

Manufacture of Meat Products Using Nitrite-Containing Composition and Confirmation of Color Development

[2-1] Preparation of Model Meat Products

Using the fermented spinach powder prepared through Example 1, model meat products were manufactured by mixing pork hind leg meat with pork fat in proportions shown in Table 6. Preparation Examples 1 and 2 were prepared by adding the fermented spinach powder of Example 1 in concentrations of 20 ppm and 100 ppm, respectively, Comparative Preparation Example 1 was prepared without adding nitrite (negative control), and Comparative Preparation Examples 2 and 3 were prepared by adding synthetic nitrite in concentrations of 20 ppm and 100 ppm, respectively (positive controls). The fermented spinach powder was added to the meat products of Preparation Examples 1 and 2 in amounts of 0.03% and 0.149%, respectively, based on 100,000 ppm.

TABLE 6

| Raw material | Comparative Preparation Example 1 | Comparative Preparation Example 2 (20 ppm) | Comparative Preparation Example 3 (100 ppm) | Preparation Example 1 (20 ppm) | Preparation Example 2 (100 ppm) |
|---|---|---|---|---|---|
| Pork | 60.00 | 60.00 | 60.00 | 60.00 | 60.00 |
| Pork fat | 20.00 | 20.00 | 20.00 | 20.00 | 20.00 |
| Purified water | 16.70 | 16.70 | 16.70 | 16.60 | 16.50 |
| Soy protein isolate | 2.00 | 2.00 | 2.00 | 2.00 | 2.00 |
| Refined salt | 1.00 | 1.00 | 1.00 | 1.00 | 1.00 |
| Phosphate | 0.30 | 0.30 | 0.30 | 0.30 | 0.30 |
| Synthetic nitrite | | 0.002 | 0.01 | | |
| Fermented spinach powder | | | | 0.030 | 0.149 |
| Total | 100 | 100 | 100 | 100 | 100 |

As a result, in the case of the powders prepared through the spray drying, it was found that the lower the proportion of maltodextrin as the excipient, the larger the amount of nitrite. It was confirmed that when the amount of the excipient was small, the overall solid content decreased, and the yield also decreased. When the amount of an excipient is large, as the excipient is incorporated in a large amount, the total solid content may increase, and the fluidity of the spinach concentrate may decrease, resulting in differences in evaporation rates, leading to limitations on productivity. In contrast, the powder prepared through the lyophilization may have lower productivity and yield than the powder

[2-2] Measurement of Chromaticities of Nitrite-Added Meat Products

For the model meat products of Preparation Examples 1 and 2 and Comparative Preparation Examples 1 to 3, the appearances were observed and the chromaticities were measured. The meat products were pulverized with a blender and then put in a Petri dish, followed by performing measurement three times to measure Hunter L, a, and b values. For the surface color, a chromameter (CR-400, Minolta Co., Japan) calibrated with a standard white plate (L=97.40, a=−0.49, b=1.96) was used. Based on the measured L, a, and b values, color difference (ΔE) values were calculated and analyzed for comparison (Table 7). *ΔE is the color difference from Comparative Preparation Example 1 (negative control), and **ΔE is the color difference from Comparative Preparation Example (positive control) of the same nitrite concentration.

TABLE 7

| Treatment group | L | a | b | *ΔE | **ΔE |
|---|---|---|---|---|---|
| Comparative Preparation Example 1 | 68.43 | 4.36 | 10.04 | | |
| Comparative Preparation Example 2 (20 ppm) | 67.46 | 6.36 | 8.49 | 2.71 | |
| Preparation Example 1 (20 ppm) | 67.85 | 7.69 | 8.26 | 3.81 | 1.40 |
| Comparative Preparation Example 3 (100 ppm) | 68.34 | 7.84 | 8.25 | 3.91 | |
| Preparation Example 2 (100 ppm) | 67.69 | 6.82 | 8.18 | 3.17 | 1.21 |

As a result of observing the appearances of the model meat products, the reddish color was barely observed in the negative control, Comparative Preparation Example 1, in which nitrite was not added, whereas the reddish color was observed in Preparation Examples 1 and 2 and Comparative Preparation Examples 2 and 3 even with naked eyes, compared to Comparative Preparation Example 1 (FIGURE). As a result of measuring the chromaticities, the difference in brightness between the meat products of Preparation Examples 1 and 2 and Comparative Preparation Examples was not large, and in the case of redness, except for Comparative Preparation Example 1 in which nitrite was not added, similar patterns were observed in Preparation Examples 1 and 2 and Comparative Preparation Examples 2 and 3. Even in the case of the color difference ΔE value, there was a big difference from the negative control, Comparative Preparation Example 1, whereas there was no significant difference in color difference values between the positive controls and Preparation Examples 1 and 2.

Based on the above results, it was confirmed that although the fermented spinach powder prepared without using reducing bacteria was added to the meat products, the meat products had a color development effect at a level similar to that of meat products to which synthetic nitrite was added.

[2-3] Measurement of Residual Nitrite Ions

The amounts of residual nitrite ions in the model meat products of Preparation Examples 1 and 2 and Comparative Preparation Examples 1 to 3 were measured by using the diazotization method. 0.5 N sodium hydroxide, 12% zinc sulfate, pH 9.0 ammonium acetate, and distilled water were added to 10 g of each sample, followed by homogenization, heating, and filtration processes to prepare a test solution. A sulfanilamide solution, a N-(1-naphthyl)ethylenediamine solution, and distilled water were added to the prepared test solution and reacted for 20 minutes. A spectrophotometer was used to measure, at a wavelength of 540 nm, the absorbance which was then substituted into a calibration curve to calculate the amount (μg) of nitrite ion included in 20 mL of the test solution. Based on this, the concentrations of nitrite ions were calculated and are shown in Table 8. It is expected that the fermented spinach powder may be used in a minimum amount such that a color development effect may be sufficiently exhibited, and at the same time, residual nitrite ion may be minimized.

TABLE 8

| | Comparative Preparation Example 1 | Comparative Preparation Example 2 (20 ppm) | Comparative Preparation Example 3 (100 ppm) | Preparation Example 1 (20 ppm) | Preparation Example 2 (100 ppm) |
|---|---|---|---|---|---|
| Nitrite ion (ppm) | 0 | 4.0 | 35.0 | 8.0 | 27.0 |

Example 3

Analysis of Components in Nitrite-Containing Composition According to the Present Application It was confirmed whether any component other than nitrite was included in the fermented spinach prepared through Example 1. A sample (hereinafter, "fermented spinach") prepared by squeezing spinach and performing fermentation through pH control in Example 1-1, a sample (hereinafter, "fermented spinach concentrate") subjected to inactivation and concentration processes as in Example 1-2, and a powder sample (hereinafter, "fermented spinach powder") prepared through a lyophilization process as in Example 1-2 were used, and a fermented plant (hereinafter, "fermented reducing bacteria") prepared by a conventional technique by inoculating nitrite reducing bacteria was used as a control. The conventional fermented plant was prepared by mixing dried celery powder with purified water and then inoculating reducing bacteria (*Staphylococcus camosus*) to perform fermentation.

[3-1] Analysis of Amino Acids

The types and amounts of amino acids contained in the fermented spinach, fermented spinach concentrate, and fermented spinach powder of the present application and the fermented reducing bacteria prepared through the conventional technique of the related art were measured (Table 9).

Specifically, 9.9 mL of distilled water was added to 0.1 mL of each sample solution, thoroughly mixed, and then centrifuged (10,000 rpm, 10 minutes, 4° C.), and the supernatant was filtered through a 0.25 μm syringe filter. Amino acids of the filtrate were analyzed using an amino acid analyzer (high-speed amino acid analyzer, L-8900, Hitachi Co., Japan) under the following analysis conditions. A column used was 2622SC-PH ion exchange column (4.6×60 mm, Hitachi, Co., Japan). The mobile phase was in a gradient mode, and pump 1 pumped sodium acetate buffers (MCI buffer PH1, PH4, RG) at a column temperature of 57° C. and a flow rate of mL/min, and pump 2 pumped ninhydrin solutions (R1, R2) at a flow rate of 0.35 mL/min. The injection volume was 10 μL, and a detector used was a dual-channel detector with channel 1: UV-570 nm and channel 2: UV-440 nm.

TABLE 9

| (ppm) | Fermented spinach | Fermented spinach concentrate | Fermented spinach powder | Fermented reducing bacteria |
|---|---|---|---|---|
| Aspartic acid | 27.03 | 68.85 | 402.99 | 31.70 |
| Threonine | 38.17 | ND | ND | 47.54 |
| Serine | 39.52 | Trace | 393.96 | 75.88 |
| Glutamic acid | 179.20 | 893.71 | 3,893.06 | 145.56 |
| Glycine | 30.93 | 159.99 | 492.11 | ND |
| Cysteine | ND | ND | ND | ND |
| Alanine | 62.52 | 535.07 | 1,693.99 | 18.85 |
| Valine | 109.11 | 891.48 | 2,710.17 | 32.81 |
| Methionine | 28.99 | Trace | 374.73 | ND |
| Isoleucine | 47.83 | 593.67 | 1,322.64 | ND |
| Leucine | 100.64 | 1,243.50 | 2,487.55 | ND |
| Tyrosine | 50.69 | Trace | 1,366.18 | ND |
| Phenylalanine | 134.44 | 2,362.49 | 3,318.69 | 74.82 |
| Lysine | 59.82 | 370.57 | 1,077.16 | ND |
| Histidine | ND | ND | ND | ND |
| Arginine | 12.73 | ND | ND | ND |

As a result, it was found that a total of 14 amino acids were produced and included in the samples such as the fermented spinach prepared in Example 1 of the present application, and some amino acids among them were modified during the concentration and drying processes or converted to other types of compounds during the metabolic process, resulting in some differences in the fermented spinach concentrate and the fermented spinach powder. Threonine was present in the control, fermented reducing bacteria, prepared with the technique of the related art by inoculating reducing bacteria, whereas threonine was not present in the samples such as the fermented spinach prepared through Example 1. In addition, glycine, methionine, isoleucine, leucine, tyrosine, lysine, and arginine were not detected in the fermented reducing bacteria, whereas all of the amino acids were detected in the fermented spinach of the present application, and all amino acids except for arginine were also detected in the fermented spinach concentrate and the fermented spinach powder. It was confirmed that the samples such as the fermented spinach included a large amount of amino acids such as aspartic acid and glutamic acid in addition to glycine, wherein glycine, aspartic acid, and glutamic acid are known as amino acids for umami, and thus, the nitrite-containing composition of the present application including such amino acids, when applied to meat or the like, may have positive effects not only in terms of color development but also in terms of taste.

Given the above result, it was confirmed that there was a clear difference between the fermented product prepared by inoculating reducing bacteria and the composition of the present application prepared by activating reductase of the spinach without reducing bacteria in terms of the composition of the amino acids included in the final composition due to the different preparing methods.

[3-2] Analysis of Nucleic Acid-Based Compounds

The types and amounts of nucleic acid-based compounds contained in the fermented spinach, fermented spinach concentrate, and fermented spinach powder of the present application and the fermented reducing bacteria prepared through the technique of the related art were measured (Table 10).

Specifically, 200 μL of each sample solution in the filtered liquid state was obtained through centrifugation and injected into high-speed liquid chromatography (HPLC) device (HPLC, Waters, Milford, MA, U.S.A./Pump: Waters 510, Injector: Waters 712 WISP) to analyze the nucleic acid-based compounds. A UV detector (254 nm, Waters, Milford, MA, U.S.A.) and μ-Bondapack column (3.9×300 mm) were used, and the analysis temperature of the column was 30° C. A 1% triethylamine solution adjusted to pH 6.5 using phosphoric acid was used as a mobile phase solution, and the speed was 1 mL/min.

TABLE 10

| (ppm) | Adenine | Hypoxanthine | AMP.2 Na | Guanosine | Xanthine | Inosine | Xanthosine | IMP.2 Na · 7.5 $H_2O$ |
|---|---|---|---|---|---|---|---|---|
| Fermented spinach | ND | Trace | ND | Trace | 35.54 | 0.47 | 0.53 | 7.67 |
| Fermented spinach concentrate | ND | 377.0 | ND | 45.0 | 577.0 | 115.0 | ND | ND |
| Fermented spinach powder | ND | 984.0 | ND | 85.0 | 1,387.0 | 176.0 | ND | ND |
| Fermented reducing bacteria | 2.26 | ND | 11.8 | ND | ND | ND | ND | ND |

As a result, adenine and AMP.2Na were detected in the fermented reducing bacteria prepared by inoculating reducing bacteria, but not detected in the fermented spinach, the fermented spinach concentrate, or the fermented spinach powder. In addition, it was confirmed that nucleic acid-based compounds such as hypoxanthine, guanosine, xanthine, inosine, xanthosine, and IMP.2Na·7.5$H_2O$, which were not detected in the fermented reducing bacteria, were produced and present in the fermented spinach, the fermented spinach concentrate, or the fermented spinach powder. It was confirmed that some compounds were included only in the fermented spinach and were removed during the concentration and drying processes, but hypoxanthine, guanosine, xanthine, and inosine increased in concentration.

Given the above result, it was confirmed that there was a clear difference between the fermented product prepared by inoculating reducing bacteria and the composition of the present application prepared by activating reductase of the spinach without reducing bacteria in terms of the types or amounts of the nucleic acid-based compounds included in the final composition since metabolic processes are different depending on whether the reducing bacteria were inoculated.

[3-3] Analysis of Organic Acids

The types and amounts of organic acids contained in the fermented spinach, fermented spinach concentrate, and fermented spinach powder of the present application and the fermented reducing bacteria prepared through the technique of the related art were measured (Table 11).

Specifically, 9.9 mL of distilled water was added to 0.1 mL of each sample solution, thoroughly mixed, and then centrifuged (10,000 rpm, 10 minutes, 4° C.), and the supernatant was filtered through a 0.25 μm syringe filter. Thermo Scientific Dionex ICS-3000 system was used to measure the types and amounts of organic acids contained in each sample solution, and the analysis was performed under the following conditions. A column used was aminex HPX-87H ion exclusion column (7.8×300 mm; Bio-Rad, Hercules, CA, U.S.A.). The mobile phase was in a gradient mode, and a solution of 0.005N sulfuric acid and acetonitrile (95:5, v/v) was flowed at a flow rate of 0.6 mL/min at a temperature of 33° C. and injected in an amount of 25 μL. A detector used was a Conductivity Detector.

TABLE 11

| | Citric acid | Malic acid | Succinic acid | Lactic acid | Acetic acid |
|---|---|---|---|---|---|
| Fermented spinach | ND | ND | 125.7 | ND | 1,027.1 |
| Fermented spinach concentrate | Trace | Trace | 723.1 | Trace | 12,402.9 |
| Fermented spinach powder | 2,360.4 | 1,966.9 | 5,349.2 | 1,203.4 | 45,393.7 |
| Fermented reducing bacteria | 87.0 | 1,274.2 | 29.2 | 149.3 | 243.7 |

As a result, adenine and AMP.2Na were detected in the fermented reducing bacteria prepared by inoculating reducing bacteria, but not detected in the fermented spinach, the fermented spinach concentrate, or the fermented spinach powder. In addition, it was confirmed that nucleic acid-based compound such as hypoxanthine, guanosine, xanthine, inosine, xanthosine, and IMP.2Na·7.5$H_2O$, which were not detected in the fermented reducing bacteria, were produced and present in the fermented spinach, the fermented spinach concentrate, or the fermented spinach powder. It was confirmed that some compounds were included only in the fermented spinach and were removed during the concentration and drying processes, but hypoxanthine, guanosine, xanthine, and inosine increased in concentration.

Given the above result, it was confirmed that there was a clear difference between the fermented product prepared by inoculating reducing bacteria and the composition of the present application prepared by activating reductase of the spinach without reducing bacteria in terms of the types or amounts of the nucleic acid-based compounds included in the final composition since metabolic processes are different depending on whether the reducing bacteria were inoculated.

[3-4] Analysis of Free Sugars

The types and amounts of free sugars contained in the fermented spinach, fermented spinach concentrate, and fermented spinach powder of the present application and the fermented reducing bacteria prepared through the technique of the related art were measured (Table 12).

Specifically, 9.9 mL of distilled water was added to 0.1 mL of each sample solution, thoroughly mixed, and then centrifuged (10,000 rpm, 10 minutes, 4° C.), and the supernatant was filtered through a 0.25 μm syringe filter. Dionex ICS-5000 system was used to measure the types and amounts of free sugars contained in each sample solution, and the following analysis was performed. Columns used were CarboPac PA1 guard column (Dionex, 50×4 mm) and CarboPac PA1 analytical column (Dionex, 250×4 mm) maintained at 30° C. A mobile phase A solution used was 400 mM NaOH, and a mobile phase B solution used was pure water. In a gradient mode, 0 min, 95% B, 5 min, 0% B, 30 min, 10% B, 30.1 min, 95% B, and 40 min, 95% B were flowed at a flow rate of 1.0 mL/min and injected in an amount of 5 μL. A detector used was ECD.

TABLE 12

| | Trehalose | Fructose | Glucose | Sucrose | Lactose |
|---|---|---|---|---|---|
| Fermented spinach | 12.45 | 27.63 | ND | ND | Trace |
| Fermented spinach concentrate | ND | ND | ND | ND | 230.5 |
| Fermented spinach powder | ND | ND | ND | ND | 793.6 |
| Fermented reducing bacteria | ND | 1,370.9 | 1,868.9 | 2,756.4 | ND |

As a result, trehalose and lactose, which were not detected in the fermented reducing bacteria, were present in the fermented spinach, and in particular, lactose was included even in the fermented spinach concentrate and the fermented spinach powder, which had been subjected to the filtration and drying processes. In addition, as a result of the fermentation using the reducing bacteria, glucose and sucrose were present in extremely large amounts, but were not detected at all in the fermented spinach.

The fermented product prepared by inoculating reducing bacteria contains a large amount of reducing sugars as described above, and thus, may cause browning and negatively affect the appearance when applied to products to be sterilized at high temperatures. In contrast, the nitrite-containing composition of the present application has an excellent color development effect attributed to nitrite and has an effect of minimizing browning because a small amount of reducing sugars is included, and thus, when applied to meat products, may have an excellent synergistic effect in terms of improvement of the appearance quality.

[3-5] Analysis of γ-Aminobutyric Acids (GABA)

The amounts of γ-aminobutyric acids (GABA) contained in the fermented spinach, fermented spinach concentrate, and fermented spinach powder of the present application and the fermented reducing bacteria prepared through the technique of the related art were measured (Table 13).

Specifically, Water's AccQ Fluor™ reagent kit was used for derivatization for analysis. A reaction reagent was prepared by dissolving 1 mL of acetonitrile (vial 2B) in 6-aminoquinolyl-n-hydroxysuccinimidyl carbamate (vial 2A). 70 μL of a borate buffer solution (vial 1) was added to 10 μL of a standard solution and extract, vortexed, and then left at room temperature for 1 minute. After 20 μL of the reaction reagent was added and vortexed, the mixture was reacted in a water bath at 55° C. for 10 minutes. After completion of the reaction, the mixture was cooled to room temperature and analyzed using HPLC (Waters 2690 system). A column used was Mightysil RP-18 GP column (4.6×250 mm, 5 μm, Kanto Chemical, Tokyo, Japan), a mobile phase A was obtained by diluting 200 mL of AccQ-Tag Eluent A concentrate in 2 L of HPLC water, and a mobile phase B used was AccQ-Tag Eluent B. Solvent composition was analyzed by gradient elution with an initial A:B maintained at 90:10, followed by 70:30 (0.6 mL/min)

by 30 minutes, 0:100 (0.8 mL/min) by 31 minutes, 0:100 (0.8 mL/min) by 38 minutes, 90:10 (0.6 mL/min) by 39 minutes, and 90:10 (0.6 mL/min) by 50 minutes. The sample injection amount was 10 μL, and a detector used was a fluorescence detector (474, Waters) with Ex. 250 nm and Em. 395 nm for analysis.

TABLE 13

| | Fermented spinach | Fermented spinach concentrate | Fermented spinach powder | Fermented reducing bacteria |
|---|---|---|---|---|
| GABA (mg/L) | 54.0 | 940.0 | 2,150.0 | 10.0 |

As a result, it was confirmed that the fermented spinach contained at least 5 times higher concentration of GABA than the fermented product prepared using reducing bacteria, and the fermented spinach concentrate and the fermented spinach powder contained even larger amounts of GABA. It seemed that GABA was produced because some glutamic acid was reduced during the metabolic process when the spinach was fermented, and the fermented reducing bacteria included GABA in a concentration of 10 mg/L, which is not high, which is interpreted as a result of nitrite being produced through a different metabolic process.

In the above, although representative embodiments of the present application have been exemplarily described, the scope of the present application is not limited to specific embodiments as described above, and those skilled in the art will be able to make appropriate changes within the scope described in the claims of the present application.

The invention claimed is:

1. A method of producing natural nitrite, comprising:

preparing an extract from a plant containing nitrate;

activating endogenous nitrate reductase within the plant extract; and inactivating the nitrate reductase, wherein the activating of the nitrate reductase comprises adding the plant extract into a phosphate buffer solution or a carbonate buffer solution and maintaining the pH of the buffer solution containing the plant extract within a range of pH 6 to pH 9 at a temperature of 20 to 40° C., wherein the inactivating of the nitrate reductase comprises heating the buffer solution containing the plant extract to a temperature of 60° C. or higher, and wherein the plant comprises nitrate in a concentration of 3,000 ppm or more.

2. The method of claim 1, wherein the plant is at least one selected from the group consisting of spinach, lettuce, Chinese cabbage, head lettuce, cabbage, young radish, sesame leaf, chicory, radish leaf, radish, crown daisy, kale, leaf mustard, leek, water parsley, and red beet.

3. The method of claim 1, wherein the extract is obtained by squeezing or crushing the plant.

4. The method of claim 1, wherein the phosphate buffer solution is a buffer solution comprising $NaH_2PO_4$ and $Na_2HPO_4$, and the carbonate buffer solution is a buffer solution comprising $Na_2CO_3$ and $NaHCO_3$.

5. The method of claim 1, wherein the inactivating of the nitrate reductase comprises heating the plant extract to a temperature of 60° C. to 95° C.

6. The method of claim 1, further comprising drying the plant extract after the inactivating of the nitrate reductase.

7. The method of claim 6, wherein the drying of the plant extract comprises lyophilization or spray drying.

* * * * *